United States Patent [19]

Yoshida et al.

[11] Patent Number: 4,675,412
[45] Date of Patent: Jun. 23, 1987

[54] PROCESS FOR PREPARING 5-MERCAPTO-1,2,3-THIADIAZOLE SALTS

[75] Inventors: Hiroshi Yoshida; Teruhiko Inoue, both of Ube, Japan

[73] Assignee: Ube Industries, Ltd., Ube, Japan

[21] Appl. No.: 777,834

[22] Filed: Sep. 19, 1985

[30] Foreign Application Priority Data

Sep. 28, 1984 [JP] Japan .................. 59-201841

[51] Int. Cl.⁴ ........................... C07D 285/06
[52] U.S. Cl. .................................. 548/127
[58] Field of Search ........................ 548/127

[56] References Cited

U.S. PATENT DOCUMENTS 4,540,794 9/1985 Sakai .................. 548/127

Primary Examiner—Robert Gerstl
Attorney, Agent, or Firm—Frishauf, Holtz, Goodman & Woodward

[57] ABSTRACT

There is disclosed a process for preparing 5-mercapto-1,2,3-thiadiazole salts comprising reacting a hydrazone compound represented by the formula:

$$X_3C-CH=N-NH-SO_2Ar$$

wherein X represents a halogen atom and Ar represents an aryl group, with a polysulfide compound represented by the formula:

$$M_2S_x$$

wherein M represents an alkali metal atom or an $NH_4$ group and x is an integer of 2 to 6.

The present invention provides the 5-mercapto-1,2,3-thiadiazole salt with remarkably increased yield as compared with the conventional method.

12 Claims, No Drawings

PROCESS FOR PREPARING 5-MERCAPTO-1,2,3-THIADIAZOLE SALTS

BACKGROUND OF THE INVENTION

This invention relates to a process for preparing 5-mercapto-1,2,3-thiadiazole salts.

A 5-mercapto-1,2,3-thiadiazole salt is a chemical material having a wide application as an intermediate for pharmaceuticals, agricultural chemicals and so on, particularly as an important compound for a modifier of antibiotics.

Heretofore, as a process for preparing 5-mercapto-1,2,3-thiadiazole salt, there have been known, for example, (1) a method in which chloroacetaldehyde ethoxycarbonylhydrazone is subjected to reaction with thionyl chloride followed by the mercaptization reaction of the resulting product [Japanese Provisional Patent Publication No. 23974/1978]:

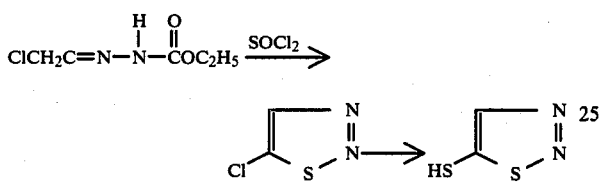

or a method which uses a diazo compound [Tetrahedron Letters, Vol. 26, p. 2389 (1973)]:

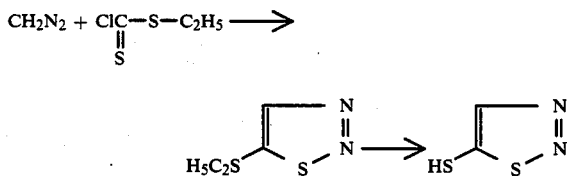

(2) a method in which a trihaloacetaldehyde and a hydrazine are subjected to a condensation reaction in a solvent, followed by the reaction of the resulting reaction product with a salt of a sulfide or a salt of a hydrosulfide compound [Japanese Provisional Patent Publication No. 95282/1984] or a method in which a hydrazone compound is subjected to the reaction with a sulfide compound represented by the formula: MM′S (wherein M is an alkali metal atom and M′ is a hydrogen atom or an alkali metal) such as a reaction product of trichloroacetaldehyde-p-toluenesulfonylhydrazone and sodium sulfide [Japanese Provisional Patent Publication No. 51271/1984 which corresponds to European Patent application No. 103840]:

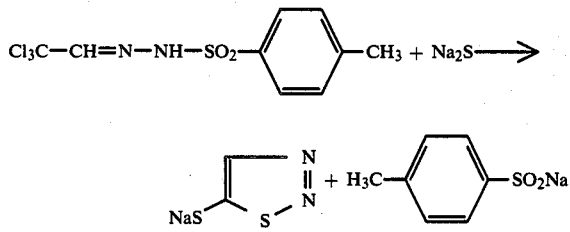

and the like.

However, in the method of (1), there exist problems that the starting materials are unstable and hence accompanied by difficulties in handling thereof, and in the method of (2), a yield of the 5-mercapto-1,2,3-thiadiazole salt which is the intended compound is low and they were not the industrially advantageous processes.

SUMMARY OF THE INVENTION

The present inventors have carried out earnest studies to establish a process for producing a 5-mercapto-1,2,3-thiadiazole which is industrially advantageous. As a result, the present inventors have found that the purpose of the present invention can be attained by replacing the sulfide in the aforesaid process (2) with a polysulfide compound as a reactive reagent for a cyclization reaction of a hydrazone compound, and have found that yield of the intended compound has increased with great extent and thus have accomplished the present invention.

The reaction of the present invention can be shown by the following formula:

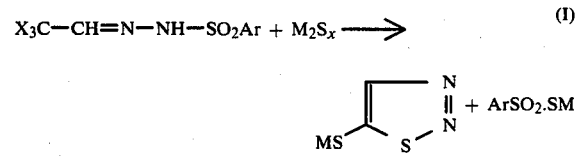

(I)

wherein X represents a halogen atom, Ar represents an aryl group, M represents an alkali metal atom or an $NH_4$ group and x is an integer of 2 to 6.

That is, a process for preparing a 5-mercapto-1,2,3-thiadiazole salt of the present invention comprises reacting a hydrazone compound represented by the formula:

$$X_3C-CH=N-NH-SO_2Ar \quad \text{(II)}$$

wherein X and Ar have the same meanings as defined in the above formula (I), with a polysulfide compound represented by the formula:

wherein M and x have the same meanings as defined in the above formula (I).

DESCRIPTION OF THE PREFERRED EMBODIMENTS

The hydrazone compound represented by the formula (II) to be used in the present invention can be easily obtained by conventionally well-known methods such as, for example, a method as described in the literature (K. Bott, Chem. Ber., 1975, Vol. 108, p. 402), a method as disclosed in Japanese Provisional Patent Publication No. 95282/1984 and the like. Representative examples of the hydrazone compounds represented by the formula (II) may include trichloroacetaldehyde-p-toluenesulfonylhydrazone, tribromoacetaldehyde-p-toluenesulfonylhydrazone, triiodoacetaldehyde-p-toluenesulfonylhydrazone, trichloroacetaldehyde-benzenesulfonylhydrazone and the like. These hydrazone compounds represented by the formula (II) may be used for cyclization reaction after isolation from the reaction mixture in which there has been formed a hydrazone compound. However, as disclosed in the above Japanese Provisional Patent Publication No. 95282/1984, a method in which a trihaloacetaldehyde is subjected to the condensation reaction with an arylsulfonylhydrazine in a solvent, followed by the cyclization reaction of the reaction mixture which contains a hydrazone compound represented by the formula (II) can be utilized without isolation therefrom with the polysulfide compound to obtain an intended compound, is preferred since the procedures can be simplified, there is no loss of the reaction product which loss accompanies the isolation operation and the solvent used in the condensation reaction can effectively be utilized as the solvent for the cyclization reaction as it is.

As the polysulfide compound represented by the formula (III) to be used for formation of a 5-mercapto-1,2,3-thiadiazole salt by cyclization reaction of the hydrazone compound represented by the formula (II), there may be mentioned, for example, sodium disulfide, sodium trisulfide, sodium tetrasulfide, sodium pentasulfide, sodium hexasulfide, potassium disulfide, potassium trisulfide, potassium tetrasulfide, potassium pentasulfide, potassium hexasulfide, ammonium disulfide, ammonium trisulfide, ammonium tetrasulfide, ammonium pentasulfide, ammonium hexasulfide and the like. These polysulfides can be prepared by, for example, (1) a method as described in New Experimental Chemistry Lecture, Vol. 8, p. 382, published by Maruzen Co. (1976); Acta. Cryst. B29, p. 1463 (1963); or Acta. Chem. Scand., Vol. 25, p. 3329 (1971), (2) a method in which sodium sulfide, potassium sulfide and the like are subjected to the reaction with simple sulfur (sulfur simple substance) in a hydrous alcohol until the simple sulfur has been dissolved as described in Org. Syn., Coll. Vol. 1, p. 221 (1956), (3) a method in which sodium sulfide, potassium sulfide, ammonium sulfide or the like is subjected to the reaction with simple sulfur in water or a lower alcohol such as methanol and ethanol until the simple sulfur has been dissolved, or the like.

When the cyclization reaction of the hydrazone compound represented by the formula (II) has been carried out by using the polysulfide compound represented by the formula (III), a method in which the cyclization reaction is carried out by adding a polysulfide-containing solution in which is formed a polysulfide compound by the aforesaid method (2) or (3) to the solution containing a hydrazone compound, for example, a reaction mixture obtained by said cyclization reaction or a solution formed by disolving hydrazone compound in a solvent; a method in which the cyclization reaction is carried out by adding the hydrazone compound to a polysulfide compound-containing solution; a method in which the cyclization reaction is carried out by adding simple sulfur to a solution containing a hydrazone compound, followed by addition of a sulfide compound such as sodium sulfide, potassium sulfide, ammonium sulfide or the like to form a polysulfide in the reaction system; or the like can be employed. The polysulfide represented by the formula (III) may preferably be used, in general, in an amount of 2 to 8 moles based on a mole of the hydrazone compound, more preferably 3 to 5 moles.

In order to carry out the present invention, the cyclization reaction may preferably be carried out in a solvent, and as the solvent, there may be used water; a lower alcohol such as methyl alcohol, ethyl alcohol, isopropyl alcohol, t-butyl alcohol and the like; an aromatic hydrocarbon such as benzene, xylene, toluene and the like; a halogenated hydrocarbon such as methylene chloride, chloroform and the like; and mixtures of the above, among them, water, the lower alcohol and the like are particularly preferred.

Further, for carrying out the present invention, it is preferred that the pH of the reaction system is maintained in the range of 10 to 11 for carrying out the cyclization reaction. By adjusting and maintaining the pH of the reaction system within 10 to 11, side reactions such as a hydrolysis reaction of the hydrazone compound can be restrained whereby a yield of the 5-mercapto-1,2,3-thiadiazole salt to be obtained can be further increased. As the pH adjusting agent, an acid or a base may optionally be used. As the acid, there may be mentioned a mineral acid such as hydrochloric acid, sulfuric acid, phosphoric acid and the like; and an organic acid such as acetic acid, p-toluenesulfonic acid and the like, and as the base, there may be mentioned sodium hydroxide, potassium hydroxide, ammonia and the like.

In the present invention, the cyclization reaction may be carried out by any of methods such as a batch system, a continuous system and the like. The reaction temperature at which the cyclization reaction is carried out is $-10°$ to 60° C., preferably 10° to 40° C., and the reaction time is not particularly limited, but generally the reaction is completed after 1 to 5 hours and a 5-mercapto-1,2,3-thiadiazole salt is formed.

Isolation of the 5-mercapto-1,2,3-thiadiazole salt from the reaction mixture can be easily carried out by removing a precipitate of an inorganic salt by-produced by the reaction and then condensing the reaction mixture to distill out the solvent and by separating crystals from the condensate, and according to the conventional manner, if desired, a 5-mercapto-1,2,3-thiadiazole salt having high purity can be obtained by recrystallizing the obtained crystals.

EXAMPLES

EXAMPLE 1

In 20 ml of methanol were dissolved 3.98 g (24 mmole) of chloral hydrate and 3.72 g (20 mmole) of p-toluenesulfonylhydrazine, and the mixture was stirred at room temperature for 40 minutes to form trichloroacetaldehyde-p-toluenesulfonylhydrazone.

On the other hand, 11.1 g (66 mmole) of sodium sulfide pentahydrate, 2.11 g (66 mmole) of sulfur simple substance and 4.8 g of water were heated to 50° to 60° C. and the heating was ceased when the mixture was a homogeneous solution to form sodium disulfide. The thus prepared solution of sodium disulfide was added to the previously prepared reaction solution of trichloroacetaldehyde-p-toluenesulfonylhydrazone for about 10 minutes while maintaining the pH of the reaction mixture within 10 to 11, and furhter stirring was continued for 4 hours while maintaining the pH of the reaction system within 10 to 11 by using a 30% by weight aqueous sodium hydroxide solution. After completion of the reaction, precipitated inorganic compounds such as sodium chloride were removed by filtration. A part of the filtrate was sampled and analyzed with the internal standard method by using liquid chromatography. A yield of the obtained product to the starting p-toluenesulfonylhydrazine was as follows.

Yield of sodium salt of 5-mercapto-1,2,3-thiadiazole was 73%.

EXAMPLE 2

In 20 ml of methanol were dissolved 0.99 g (6 mmole) of chloral hydrate and 0.93 g (5 mmole) of p-toluenesulfonylhydrazine, and the mixture was stirred at room temperature for 30 minutes to form trichloroacetaldehyde-p-toluenesulfonylhydrazone.

On the other hand, 3.96 g (16.5 mmole) of sodium sulfide nonahydrate, 2.11 g (66 mmole) of sulfur simple substance and 20 g of water were dissolved under room temperature and stirring was continued until the mixture became a homogeneous solution to form sodium pentasulfide. The thus prepared solution of sodium pentasulfide was added to the previously prepared reaction solution of tri-chloroacetaldehyde-p-toluenesulfonylhydrazone for 1 minute, and stirring was continued for 2 hours while maintaining the pH of the reaction system within 10 to 11 by using a 30 % by weight aqueous sodium hydroxide solution. The analysis after completion of the reaction was carried out in the same manner as in Example 1. A yield of the obtained product to the starting p-toluenesulfonylhydrazine was as follows.

Yield of sodium salt of 5-mercapto-1,2,3-thiadiazole was 78%.

COMPARATIVE EXAMPLE 1

In 40 ml of a 50% hydrous methanol were dissolved 3.96 g (16.5 mmole) of sodium sulfide nonahydrate, and to the mixture was added 1.58 g (5 mmole) of a powder of trichloroacetaldehyde-p-toluenesulfonylhydrazone at once while stirring under room temperature, and reaction was carried out for 1 hour at room temperature. The pH of the reaction mixture was 14 before addition of the hydrazone and 13.8 after addition thereof. Analysis was carried out in the same manner as in Example 1. The yield of sodium salt of 5-mercapto-1,2,3-thiadiazole was 10% to the starting p-toluenesulfonylhydrazone.

COMPRATIVE EXAMPLE 2

In 20 ml of methanol were dissolved 0.91 g (5.5 mmole) of chloral hydrate and 0.93 g (5 mmole) of p-toluenesulfonylhydrazine, and the mixture was stirred at room temperature for 30 minutes to form tri-chloroacetaldehyde-p-toluenesulfonylhydrazone. Then, a solution of 3.96 g (16.5 mmole) of sodium sulfide nonahydrate dissolved in 20 ml of water was added little by little to the aforesaid solution of the hydrazone under room temperature while maintaining the pH within 10 to 11. After about 60 minutes, about 2/3 amount of the sodium sulfide solution was added thereto and the pH of the reaction mixture remained at 11.2 or less. At this time, the reaction mixture was analyzed by sampling a part thereof, a yield of sodium salt of 5-mercapto-1,2,3-thiadiazole of 40% was obtained referred to the starting p-toluenesulfonylhydrazine. Thereafter, the remainder of the sodium sulfide solution was added thereto for about 30 minutes, the ultimate pH of the solution was 12.3 and the yield of sodium salt of 5-mercapto-1,2,3-thiadiazole was 46%.

EXAMPLE 3

In 20 ml of methanol were dissolved 0.91 g (5.5 mmole) of chloral hydrate and 0.93 g (5 mmole) of p-toluenesulfonylhydrazine, and the mixture was stirred at room temperature for 60 minutes to form tri-chloroacetaldehyde-p-toluenesulfonylhydrazone. The reaction mixture was added to the solution of 2.35 g (16.5 mmole) of potassium disulfide dissolved in 20 ml of water for 20 minutes while maintaining the pH within 10 to 11 under room temperature, and the reaction was further continued while maintaining the pH of the reaction system within 10 to 11 by using an aqueous potassium hydroxide solution. The analysis after completion of the reaction was carried out in the same manner as in Example 1. A yield of the obtained product to the starting p-toluenesulfonylhydrazine was as follows.

Yield of potassium salt of 5-mercapto-1,2,3-thiadiazole was 71%.

EXAMPLE 4

In 20 ml of methanol were dissolved 0.99 g (6 mmole) of chloral hydrate and 0.93 g (5 mmole) of p-toluenesulfonylhydrazine, and the mixture was stirred at room temperature for 30 minutes to form trichloroacetaldehyde-p-toluenesulfonylhydrazone. Then, to the reaction mixture was added under room temperature 30 ml of a 5% aqueous ammonia containing 3.44 g (17.5 mmole) of ammonium pentasulfide for 15 minutes. Thereafter, the reaction was continued for further 2 hours while maintaining the pH of the reaction system at 10.4 by using a 30% by weight aqueous potassium hydroxide solution. The analysis after completion of the reaction was carried out in the same manner as in Example 1. A yield of the obtained product to the starting p-toluenesulfonylhydrazine was as follows.

Yield of potassium salt of 5-mercapto-1,2,3-thiadiazole was 68%.

COMPARATIVE EXAMPLE 3

In 20 ml of methanol were dissolved 0.99 g (6 mmole) of chloral hydrate and 0.93 g (5 mmole) of p-toluenesulfonylhydrazine, and the mixture was stirred at room temperature for 30 minutes to form trichloroacetaldehyde-p-toluenesulfonylhydrazone. Then, to the reaction mixture was added under room temperature 15 ml of a 30% hydrated methanol solution containing 1.7 g (25 mmole) of ammonium sulfide for 10 minutes. Thereafter, the reaction was continued for further 2 hours while maintaining the pH of the reaction system at 10.4 by using 28% aqueous ammonia, a 30% aqueous potassium hydroxide solution, etc. The analysis after completion of the reaction was carried out in the same manner as in Example 1. The yield of the 5-mercapto-1,2,3-thiadiazole salt referred to the starting p-toluenesulfonylhydrazine was 22%.

As seen from the above Examples and Comparative examples, by using a polysulfide compound in the cyclization reaction of the hydrazone compound, in the process of the present invention, the yield of the 5-mercapto-1,2,3-thiadiazole salt has remarkably increased with great extent as compared with the conventional method which uses a sulfide such as sodium sulfide.

We claim:

1. A process for preparing 5-mercapto-1,2,3-thiadiazole salts comprising reacting one mole of a hydrazone compound represented by the formula:

$X_3C-CH=N-NH-SO_2Ar$ wherein X represents a halogen atom and Ar represents an aryl group, with 2-8 moles of a polysulfide compound represented by the formula:

$M_2S_x$ wherein M represents an alkali metal atom or an $NH_4$ ground and x is an integer of 2 to 6, at a temperature of $-10°$ to $60°$ C. and a pH of 10-11 to form said 5-mercapto-1,2,3-thiadiazole salt.

2. A process for preparing 5-mercapto-1,2,3-thiadiazole salts according to claim 1, wherein said hydrazone compound is selected from the group consisting of trichloroacetaldehyde-p-toluenesulfonylhydrazone, tribromoacetaldehyde-p-toluenesulfonylhydrazone, triiodoacetaldehyde-p-toluenesulfonylhydrazone and tricholoroacetaldehyde-benzenesulfonylhydrazone.

3. A process for preparing 5-mercapto-1,2,3-thiadiazole salts according to claim 1, wherein said polysulfide compound is selected from the group consisting of sodium disulfide, sodium trisulfide, sodium tetrasulfide, sodium pentasulfide, sodium hexasulfide, potassium disulfide, potassium trisulfide, potassium tetrasulfide, potassium pentasulfide, potassium hexasulfide, ammonium disulfide, ammonium trisulfide, ammonium tetrasulfide, ammonium pentasulfide and ammonium hexasulfide.

4. A process for preparing 5-mercapto-1,2,3-thiadiazole salts according to claim 1, wherein the amount of the polysulfide is 3 to 5 moles based on a mole of the hydrazone compound.

5. A process for preparing 5-mercapto-1,2,3-thiadiazole salts according to claim 1, wherein the temperature of the reaction is 10° to 40° C.

6. A process for preparing 5-mercapto-1,2,3-thiadiazole salts according to claim 1, wherein the reaction time is within the range of 1 to 5 hours.

7. A process for preparing 5-mercapto-1,2,3-thiadiazole salts according to claim 1 wherein said reaction is carried out in the presence of a solvent.

8. A process for preparing 5-mercapto-1,2,3thiadiazole salts according to claim 7 wherein said solvent is a member selected from the group consisting of water, lower alcohols, aromatic hydrocarbons, halogenated hydrocarbons and mixtures thereof.

9. A process for preparing 5-mercapto1,2,3-thiadiazole salts according to claim 1, where said hydrazone is trichloroacetaldehyde-p-toluenesulfonyl hydrazone and said polysulfide is sodium disulfide.

10. A process for preparing 5-mercapto-1,2,3-thiadiazole salts according to claim 1 wherein said hydrazone is trichloroacetaldehyde-p-toluene sulfonyl hydrazone and said polysulfide is sodium pentasulfide.

11. A process for preparing 5-mercapto-1,2,3-thiadiazole salts according to claim 1 wherein said hydrazone is trichloroacetaldehyde-p-toluene sulfonyl hydrazone and said polysulfide is potassium disulfide.

12. A process for preparing 5-mercapto- b 1,2,3-thiadiazole salts according to claim 1 wherein said hydrazone is trichloroacetaldehyde-p-toulene sulfonyl hydrazone and said polysulfide is ammonium pentasulfide.

* * * * *